US009738935B2

(12) United States Patent
Liu et al.

(10) Patent No.: US 9,738,935 B2
(45) Date of Patent: Aug. 22, 2017

(54) COMPLEX MUTATIONS IN THE EPIDERMAL GROWTH FACTOR RECEPTOR KINASE DOMAIN

(71) Applicant: Roche Molecular Systems, Inc., Pleasanton, CA (US)

(72) Inventors: Wei-min Liu, Dublin, CA (US); Alison Tsan, Castro Valley, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 13/664,333

(22) Filed: Oct. 30, 2012

(65) Prior Publication Data

US 2013/0121996 A1 May 16, 2013

Related U.S. Application Data

(60) Provisional application No. 61/558,093, filed on Nov. 10, 2011.

(51) Int. Cl.
*C12Q 1/68* (2006.01)
*C07H 21/02* (2006.01)

(52) U.S. Cl.
CPC ..... *C12Q 1/6886* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| 6,582,908 B2 * | 6/2003 | Fodor et al. ............ 506/9 |
| 7,294,468 B2 * | 11/2007 | Bell et al. ............ 435/6.14 |
| 2005/0272083 A1 | 12/2005 | Seshagiri |
| 2006/0147959 A1 | 7/2006 | Bell et al. |

FOREIGN PATENT DOCUMENTS

| CN | 1749417 A | 3/2006 |
| JP | 2008502328 A | 1/2008 |
| JP | 2008545446 A | 12/2008 |
| WO | 2010077324 A | 7/2010 |
| WO | 2011069677 A | 6/2011 |
| WO | PCT/EP2012/004527 | 3/2013 |

OTHER PUBLICATIONS

Diffenbach (PCR methods and Applications (1993) vol. 3, pp. S30-S37).*
Roux et al (PCR Methods and Applications (1995) vol. 4, pp. s185-s194).*
Marchetti, Antonio, et al., 2012, "Complex Mutations & Subpopulations of Deletions at Exon 19 of EGFR in NSCLC Revealed by Next Generation Sequencing: Potential Clinical Implications", PLoS ONE, 7(7):e42164 1-8.
Wu, Jenn-Yu, et al., 2011, "Effectiveness of Tyrosine Kinase Inhibitors on "Uncommon" Epidermal Growth Factor Receptor Mutations of Unknown Clinical Significance in Non-Small Cell Lung Cancer", Clinical Cancer Research, 17 (11):3812-3821.
Smith (2008) J. Clin Pathol. 61:487.
Genbank Entry AB360371.1 (2007).

* cited by examiner

*Primary Examiner* — Katherine Salmon
(74) *Attorney, Agent, or Firm* — Carol Johns; Olga Kay

(57) ABSTRACT

Six new mutations were found in exon 19 of the EGFR gene, the exon that is often mutated in tumors. The invention comprises methods of detecting the mutations, methods of prognosis and methods of predicting response to treatment based on the presence of absence of the mutations.

4 Claims, 5 Drawing Sheets

FIGURE 1A

```
   1 ATGCGACCCTCCGGGACGGCCGGGGCAGCGCTCCTGGCGCTGCTGGCTGCGCTCTGCCCG
  61 GCGAGTCGGGCTCTGGAGGAAAAGAAAGTTTGCCAAGGCACGAGTAACAAGCTCACGCAG
 121 TTGGGCACTTTTGAAGATCATTTTCTCAGCCTCCAGAGGATGTTCAATAACTGTGAGGTG
 181 GTCCTTGGGAATTTGGAAATTACCTATGTGCAGAGGAATTATGATCTTTCCTTCTTAAAG
 241 ACCATCCAGGAGGTGGCTGGTTATGTCCTCATTGCCCTCAACACAGTGGAGCGAATTCCT
 301 TTGGAAAACCTGCAGATCATCAGAGGAAATATGTACTACGAAAATTCCTATGCCTTAGCA
 361 GTCTTATCTAACTATGATGCAAATAAAACCGGACTGAAGGAGCTGCCCATGAGAAATTTA
 421 CAGGAAATCCTGCATGGCGCCGTGCGGTTCAGCAACAACCCTGCCCTGTGCAACGTGGAG
 481 AGCATCCAGTGGCGGGACATAGTCAGCAGTGACTTTCTCAGCAACATGTCGATGGACTTC
 541 CAGAACCACCTGGGCAGCTGCCAAAAGTGTGATCCAAGCTGTCCCAATGGGAGCTGCTGG
 601 GGTGCAGGAGAGGAGAACTGCCAGAAACTGACCAAAATCATCTGTGCCCAGCAGTGCTCC
 661 GGGCGCTGCCGTGGCAAGTCCCCCAGTGACTGCTGCCACAACCAGTGTGCTGCAGGCTGC
 721 ACAGGCCCCGGGAGAGCGACTGCCTGGTCTGCCGCAAATTCCGAGACGAAGCCACGTGC
 781 AAGGACACCTGCCCCCCACTCATGCTCTACAACCCCACCACGTACCAGATGGATGTGAAC
 841 CCCGAGGGCAAATACAGCTTTGGTGCCACCTGCGTGAAGAAGTGTCCCCGTAATTATGTG
 901 GTGACAGATCACGGCTCGTGCGTCCGAGCCTGTGGGCCGACAGCTATGAGATGGAGGAA
 961 GACGGCGTCCGCAAGTGTAAGAAGTGCGAAGGGCCTTGCCGCAAAGTGTGTAACGGAATA
1021 GGTATTGGTGAATTTAAAGACTCACTCTCCATAAATGCTACGAATATTAAACACTTCAAA
1081 AACTGCACCTCCATCAGTGGCGATCTCCACATCCTGCCGGTGGCATTTAGGGGTGACTCC
1141 TTCACACATACTCCTCCTCTGGATCCACAGGAACTGGATATTCTGAAAACCGTAAAGGAA
1201 ATCACAGGGTTTTTGCTGATTCAGGCTTGGCCTGAAAACAGGACGGACCTCCATGCCTTT
1261 GAGAACCTAGAAATCATACGCGGCAGGACCAAGCAACATGGTCAGTTTTCTCTTGCAGTC
1321 GTCAGCCTGAACATAACATCCTTGGGATTACGCTCCCTCAAGGAGATAAGTGATGGAGAT
1381 GTGATAATTTCAGGAAACAAAAATTTGTGCTATGCAAATACAATAAACTGGAAAAAACTG
1441 TTTGGGACCTCCGGTCAGAAAACCAAAATTATAAGCAACAGAGGTGAAAACAGCTGCAAG
1501 GCCACAGGCCAGGTCTGCCATGCCTTGTGCTCCCCCGAGGGCTGCTGGGGCCCGGAGCCC
1561 AGGGACTGCGTCTCTTGCCGGAATGTCAGCCGAGGCAGGGAATGCGTGGACAAGTGCAAC
```

FIGURE 1B

```
1621 CTTCTGGAGGGTGAGCCAAGGGAGTTTGTGGAGAACTCTGAGTGCATACAGTGCCACCCA
1681 GAGTGCCTGCCTCAGGCCATGAACATCACCTGCACAGGACGGGGACCAGACAACTGTATC
1741 CAGTGTGCCCACTACATTGACGGCCCCACTGCGTCAAGACCTGCCCGGCAGGAGTCATG
1801 GGAGAAAACAACACCCTGGTCTGGAAGTACGCAGACGCCGGCCATGTGTGCCACCTGTGC
1861 CATCCAAACTGCACCTACGGATGCACTGGGCCAGGTCTTGAAGGCTGTCCAACGAATGGG
1921 CCTAAGATCCCGTCCATCGCCACTGGGATGGTGGGGCCCTCCTCTTGCTGCTGGTGGTG
1981 GCCCTGGGGATCGGCCTCTTCATGCGAAGGCGCCACATCGTTCGGAAGCGCACGCTGCGG
2041 AGGCTGCTGCAGGAGAGGGAGCTTGTGGAGCCTCTTACACCCAGTGGAGAAGCTCCCAAC
2101 CAAGCTCTCTTGAGGATCTTGAAGGAAACTGAATTCAAAAAGATCAAAGTGCTGGGCTCC
2161 GGTGCGTTCGGCACGGTGTATAAGGGACTCTGGATCCCAGAAGGTGAGAAAGTTAAAATT
2221 CCCGTCGCTATCAAGGAATTAAGAGAAGCAACATCTCCGAAAGCCAACAAGGAAATCCTC
2281 GATGAAGCCTACGTGATGGCCAGCGTGGACAACCCCCACGTGTGCCGCCTGCTGGGCATC
2341 TGCCTCACCTCCACCGTGCAGCTCATCACGCAGCTCATGCCCTTCGGCTGCCTCCTGGAC
2401 TATGTCCGGGAACACAAAGACAATATTGGCTCCCAGTACCTGCTCAACTGGTGTGTGCAG
2461 ATCGCAAAGGGCATGAACTACTTGGAGGACCGTCGCTTGGTGCACCGCGACCTGGCAGCC
2521 AGGAACGTACTGGTGAAAACACCGCAGCATGTCAAGATCACAGATTTTGGGCTGGCCAAA
2581 CTGCTGGGTGCGGAAGAGAAAGAATACCATGCAGAAGGAGGCAAAGTGCCTATCAAGTGG
2641 ATGGCATTGGAATCAATTTTACACAGAATCTATACCCACCAGAGTGATGTCTGGAGCTAC
2701 GGGGTGACTGTTTGGGAGTTGATGACCTTTGGATCCAAGCCATATGACGGAATCCCTGCC
2761 AGCGAGATCTCCTCCATCCTGGAGAAAGGAGAACGCCTCCCTCAGCCACCCATATGTACC
2821 ATCGATGTCTACATGATCATGGTCAAGTGCTGGATGATAGACGCAGATAGTCGCCCAAAG
2881 TTCCGTGAGTTGATCATCGAATTCTCCAAAATGGCCCGAGACCCCCAGCGCTACCTTGTC
2941 ATTCAGGGGGATGAAAGAATGCATTTGCCAAGTCCTACAGACTCCAACTTCTACCGTGCC
3001 CTGATGGATGAAGAAGACATGGACGACGTGGTGGATGCCGACGAGTACCTCATCCCACAG
3061 CAGGGCTTCTTCAGCAGCCCCTCCACGTCACGGACTCCCCTCCTGAGCTCTCTGAGTGCA
3121 ACCAGCAACAATTCCACCGTGGCTTGCATTGATAGAAATGGGCTGCAAAGCTGTCCCATC
3181 AAGGAAGACAGCTTCTTGCAGCGATACAGCTCAGACCCCACAGGCGCCTTGACTGAGGAC
```

FIGURE 1C

3241 AGCATAGACGACACCTTCCTCCCAGTGCCTGAATACATAAACCAGTCCGTTCCCAAAAGG

3301 CCCGCTGGCTCTGTGCAGAATCCTGTCTATCACAATCAGCCTCTGAACCCCGCGCCCAGC

3361 AGAGACCCACACTACCAGGACCCCCACAGCACTGCAGTGGGCAACCCCGAGTATCTCAAC

3421 ACTGTCCAGCCCACCTGTGTCAACAGCACATTCGACAGCCCTGCCCACTGGGCCCAGAAA

3481 GGCAGCCACCAAATTAGCCTGGACAACCCTGACTACCAGCAGGACTTCTTTCCCAAGGAA

3541 GCCAAGCCAAATGGCATCTTTAAGGGCTCCACAGCTGAAAATGCAGAATACCTAAGGGTC

3601 GCGCCACAAAGCAGTGAATTTATTGGAGCATGA

FIGURE 2

```
   1 MRPSGTAGAA LLALLAALCP ASRALEEKKV CQGTSNKLTQ LGTFEDHFLS
  51 LQRMFNNCEV VLGNLEITYV QRNYDLSFLK TIQEVAGYVL IALNTVERIP
 101 LENLQIIRGN MYYENSYALA VLSNYDANKT GLKELPMRNL QEILHGAVRF
 151 SNNPALCNVE SIQWRDIVSS DFLSNMSMDF QNHLGSCQKC DPSCPNGSCW
 201 GAGEENCQKL TKIICAQQCS GRCRGKSPSD CCHNQCAAGC TGPRESDCLV
 251 CRKFRDEATC KDTCPPLMLY NPTTYQMDVN PEGKYSFGAT CVKKCPRNYV
 301 VTDHGSCVRA CGADSYEMEE DGVRKCKKCE GPCRKVCNGI GIGEFKDSLS
 351 INATNIKHFK NCTSISGDLH ILPVAFRGDS FTHTPPLDPQ ELDILKTVKE
 401 ITGFLLIQAW PENRTDLHAF ENLEIIRGRT KQHGQFSLAV VSLNITSLGL
 451 RSLKEISDGD VIISGNKNLC YANTINWKKL FGTSGQKTKI ISNRGENSCK
 501 ATGQVCHALC SPEGCWGPEP RDCVSCRNVS RGRECVDKCN LLEGEPREFV
 551 ENSECIQCHP ECLPQAMNIT CTGRGPDNCI QCAHYIDGPH CVKTCPAGVM
 601 GENNTLVWKY ADAGHVCHLC HPNCTYGCTG PGLEGCPTNG PKIPSIATGM
 651 VGALLLLLVV ALGIGLFMRR RHIVRKRTLR RLLQERELVE PLTPSGEAPN
 701 QALLRILKET EFKKIKVLGS GAFGTVYKGL WIPEGEKVKI PVAIKELREA
 751 TSPKANKEIL DEAYVMASVD NPHVCRLLGI CLTSTVQLIT QLMPFGCLLD
 801 YVREHKDNIG SQYLLNWCVQ IAKGMNYLED RRLVHRDLAA RNVLVKTPQH
 851 VKITDFGLAK LLGAEEKEYH AEGGKVPIKW MALESILHRI YTHQSDVWSY
 901 GVTVWELMTF GSKPYDGIPA SEISSILEKG ERLPQPPICT IDVYMIMVKC
 951 WMIDADSRPK FRELIIEFSK MARDPQRYLV IQGDERMHLP SPTDSNFYRA
1001 LMDEEDMDDV VDADEYLIPQ QGFFSSPSTS RTPLLSSLSA TSNNSTVACI
1051 DRNGLQSCPI KEDSFLQRYS SDPTGALTED SIDDTFLPVP EYINQSVPKR
1101 PAGSVQNPVY HNQPLNPAPS RDPHYQDPHS TAVGNPEYLN TVQPTCVNST
1151 FDSPAHWAQK GSHQISLDNP DYQQDFFPKE AKPNGIFKGS TAENAEYLRV
1201 APQSSEFIGA
```

FIGURE 3

2221 CCCGTCGCTATCAAG<u>GAATTAAGAGAAGC</u>AACATCTCCGA 2260

-> CCCGTCGCTATCAAG---------*ACCC*CAACATCTCCGA

FIGURE 4

2221 CCCGTCGCTATCAAG<u>GAATTAAGA</u>GAAGCAACATCTCCGA 2260

-> CCCGTCGCTATCAAGG---*CGCCC*GAAGCAACATCTCCGA

FIGURE 5

2221 CCCGTCGCTATCAAGGAATTAAGAGAAGCAA<u>CATCTCCGAAAGCCAACAAGGAAATCCTC</u> 2280

> CCCGTCGCTATCAAGGAATTAAGAGAAGCAA------------------------*AC*CTC

FIGURE 6

2221 CCCGTCGCTATCAAGGAAT<u>TAAGAGAAGCAACATCTCCGAAAGC</u>CAACAAGGAAATCCTC 2280

> CCCGTCGCTATCAAGGAAT------------------*CGAAAGA*CAACAAGGAAATCCTC

FIGURE 7

2221 CCCGTCGCTATCAAGGAA<u>TT</u>AAGAGAAGCAACATCTCCGA 2260

-> CCCGTCGCTATCAAGGAA*CC*AAGAGAAGCAACATCTCCGA

FIGURE 8

2221 CCCGTCGCTATCAAGGAATTAAGAGAAGCAACATCTCCGAAAGC̲CAACAAGGAAATCCTC 2280

-> CCCGTCGCTATCAAGGAATTAAGAGAAGCAACATCTCCGAAAG*A*CAACAAGGAAATCCTC

SEQUENCE LISTING

```
<160> NUMBER OF SEQ ID NOS: 40

<210> SEQ ID NO 1
<211> LENGTH: 3633
<212> TYPE: DNA
<213> ORGANISM: Homo sapiens

<400> SEQUENCE: 1
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg gagctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat tccgagacga agccacgtgc     780
aaggacacct gcccccccact catgctctac aaccccacca cgtaccagat ggatgtgaac     840
cccgagggca aatacagctt tggtgccacc tgcgtgaaga gtgtccccg taattatgtg     900 gtgacagatc acggctcgtg cgtccgagcc tgtggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
```

```
ttcacacata ctcctcctct ggatccacag gaactggata ttctgaaaac cgtaaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaaactg    1440
tttgggacct ccggtcagaa aaccaaaatt ataagcaaca gaggtgaaaa cagctgcaag    1500
gccacaggcc aggtctgcca tgccttgtgc tcccccgagg gctgctgggg cccggagccc    1560
agggactgcg tctcttgccg gaatgtcagc cgaggcaggg aatgcgtgga caagtgcaac    1620
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggcccccac tgcgtcaaga cctgcccggc aggagtcatg    1800
ggagaaaaca cacccctggt ctggaagtac gcagacgccg ccatgtgtgt ccacctgtgc    1860
catccaaact gcacctacgg atgcactggg ccaggtcttg aaggctgtcc aacgaatggg    1920
cctaagatcc cgtccatcgc cactgggatg gtggggggccc tcctcttgct gctggtggtg    1980
gccctgggga tcggcctctt catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta aagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aaccccacg tgtgccgcct gctgggcatc    2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct catgatcat ggtcaagtgc tggatgatag acgcagatag tcgcccaaag    2880
ttccgtgagt tgatcatcga attctccaaa atggcccgag accccagcg ctaccttgtc    2940 attcagggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg gctgcaaag ctgtcccatc    3180 aaggaagaca gcttcttgca gcgatacagc tcagaccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac    3420 actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
```

```
gccaagccaa atggcatctt taagggctcc acagctgaaa atgcagaata cctaagggtc    3600
gcgccacaaa gcagtgaatt tattggagca tga                                 3633
```

<210> SEQ ID NO 2
<211> LENGTH: 1210
<212> TYPE: PRT
<213> ORGANISM: Homo sapiens

<400> SEQUENCE: 2

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350
```

-continued

```
Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765
```

-continued

Val Asp Asn Pro His Val Cys Arg Leu Leu Gly Ile Cys Leu Thr Ser
770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
            805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
            835                 840                 845

Gln His Val Lys Ile Thr Asp Phe Gly Leu Ala Lys Leu Leu Gly Ala
850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
            915                 920                 925

Lys Gly Glu Arg Leu Pro Gln Pro Ile Cys Thr Ile Asp Val Tyr
930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe
        1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

```
Gln Asp Phe Phe Pro Lys Glu Ala Lys Pro Asn Gly Ile Phe Lys
    1175            1180                1185

Gly Ser Thr Ala Glu Asn Ala Glu Tyr Leu Arg Val Ala Pro Gln
    1190            1195                1200

Ser Ser Glu Phe Ile Gly Ala
    1205            1210

<210> SEQ ID NO 3
<211> LENGTH: 40
<212> TYPE: DNA
<213> ORGANISM: Homo sapiens

<400> SEQUENCE: 3
cccgtcgcta tcaaggaatt aagagaagca acatctccga                    40

<210> SEQ ID NO 4
<211> LENGTH: 31
<212> TYPE: DNA
<213> ORGANISM: Homo sapiens

<400> SEQUENCE: 4
cccgtcgcta tcaagacccc aacatctccg a                             31

<210> SEQ ID NO 5
<211> LENGTH: 37
<212> TYPE: DNA
<213> ORGANISM: Homo sapiens

<400> SEQUENCE: 5
cccgtcgcta tcaaggcgcc cgaagcaaca tctccga                       37

<210> SEQ ID NO 6
<211> LENGTH: 60
<212> TYPE: DNA
<213> ORGANISM: Homo sapiens

<400> SEQUENCE: 6
cccgtcgcta tcaaggaatt aagagaagca acatctccga aagccaacaa ggaaatcctc    60

<210> SEQ ID NO 7
<211> LENGTH: 36
<212> TYPE: DNA
<213> ORGANISM: Homo sapiens

<400> SEQUENCE: 7
cccgtcgcta tcaaggaatt aagagaagca aacctc                        36

<210> SEQ ID NO 8
<211> LENGTH: 42
<212> TYPE: DNA
<213> ORGANISM: Homo sapiens

<400> SEQUENCE: 8
cccgtcgcta tcaaggaatc gaaagacaac aaggaaatcc tc                 42

<210> SEQ ID NO 9
<211> LENGTH: 40
<212> TYPE: DNA
<213> ORGANISM: Homo sapiens

<400> SEQUENCE: 9
cccgtcgcta tcaaggaacc aagagaagca acatctccga                    40
```

<210> SEQ ID NO 10
<211> LENGTH: 60
<212> TYPE: DNA
<213> ORGANISM: Homo sapiens

<400> SEQUENCE: 10
cccgtcgcta tcaaggaatt aagagaagca acatctccga aagacaacaa ggaaatcctc    60

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aattcccgtc gctatcaagg aa                                              22

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttcccgtcgc tatcaaggaa tc                                              22

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgtcgctat caaggaatcg aa                                              22

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtcgctatca aggaatcgaa agacaa                                          26

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
caacaaggaa atcctcgatg tgagt                                           25

<210> SEQ ID NO 16
<211> LENGTH: 27
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 16
gtcgctatca aggaattaag agaagca                                          27

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtcgctatca aggaattaag agaagcaaa                                        29

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
cgctatcaag gaattaagag aagcaaac                                         28

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctatcaagga attaagagaa gcaaacct                                         28

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctatcaagga attaagagaa gcaaacctc                                        29

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcgatgtgag tttctgctttt gct                                             23

<210> SEQ ID NO 22
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 22
aaagttaaaa ttcccgtcgc tatcaa                                              26

<210> SEQ ID NO 23
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agttaaaatt cccgtcgcta tcaaga                                              26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gttaaaattc ccgtcgctat caagac                                              26

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccgtcgctat caagacccca                                                     20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
caacatctcc gaaagccaac aa                                                  22

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaagttaaaa ttcccgtcgc tatcaa                                              26

<210> SEQ ID NO 28
<211> LENGTH: 28
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 28
aagttaaaat tcccgtcgct atcaaggc                                            28

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgtcgctat caaggcgc                                                       18

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
cgctatcaag gcgcccga                                                       18

<210> SEQ ID NO 31
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gaagcaacat ctccgaaagc caacaagga                                           29

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggaattaaga gaagcaacat ctccgaa                                             27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
attaagagaa gcaacatctc cgaaaga                                             27

<210> SEQ ID NO 34
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-tert-butyl-benzyl-dA

<400> SEQUENCE: 34
attaagagaa gcaacatctc cgaaaga                                              27

<210> SEQ ID NO 35
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (25)..(25)
<223> OTHER INFORMATION: N6-tert-butyl-benzyl-dA

<400> SEQUENCE: 35
attaagagaa gcaacatctc cgaaagac                                             28

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttaaaattcc cgtcgctatc aagga                                                25

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
taaaattccc gtcgctatca aggaac                                               26

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aattcccgtc gctatcaagg aacc                                                 24

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      probe
```

```
<220> FEATURE:
<221> NAME/KEY: misc_feature
<222> LOCATION: (1)..(1)
<223> OTHER INFORMATION: 5'-FAM
<220> FEATURE:
<221> NAME/KEY: modified_base
<222> LOCATION: (8)..(8)
<223> OTHER INFORMATION: BHQ2-dT
<220> FEATURE:
<221> NAME/KEY: misc_feature
<222> LOCATION: (27)..(27)
<223> OTHER INFORMATION: 3'-Phosphate

<400> SEQUENCE: 39
atggctctga acctcaggcc caccttt                                          27

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
agagcagagc agctgccaga                                                  20
```

COMPLEX MUTATIONS IN THE EPIDERMAL GROWTH FACTOR RECEPTOR KINASE DOMAIN

SEQUENCE LISTING

The instant application contains a Sequence Listing which has been submitted in ASCII format via EFS-Web and is hereby incorporated by reference in its entirety. Said ASCII copy, created on Oct. 18, 2012 is named 27475US1.txt and is 23,836 bytes in size.

FIELD OF THE INVENTION

The invention relates to cancer diagnostics and companion diagnostics for cancer therapies. In particular, the invention relates to the detection of mutations that are useful for diagnosis and prognosis as well as predicting the effectiveness of treatment of cancer.

BACKGROUND OF THE INVENTION

Epidermal Growth Factor Receptor (EGFR), also known as HER1 or ErbB1, is a member of the type 1 tyrosine kinase family of growth factor receptors. These membrane-bound proteins possess an intracellular tyrosine kinase domain that interacts with various signaling pathways. Upon ligand binding, receptors in this family undergo dimerization and subsequent autophosphorylation of the tyrosine kinase domain. The autophosphorylation triggers a cascade of events in intracellular signaling pathways, including the Ras/MAPK, PI3K and AKT pathways. Through these pathways, HER family proteins regulate cell proliferation, differentiation; and survival.

A number of human malignancies are associated with aberrant expression or function of EGFR. (Mendelsohn et al., (2000), "*The EGF receptor family as targets for cancer therapy*," Oncogene, 19:6550-6565.) In particular, it has been demonstrated that some cancers harbor mutations in the EGFR kinase domain (exons 18-21). In non-small cell lung cancer (NSCLC), these mutations were shown to promote anti-apoptotic pathways in malignant cells. (Pao et al. (2004). "*EGF receptor gene mutations are common in lung cancers from "never smokers" and are associated with sensitivity of tumors to gefitinib and erlotinib*". P.N.A.S. 101 (36): 13306-13311; Sordella et al. (2004). "*Gefitinib-sensitizing EGFR mutations in lung cancer activate anti-apoptotic pathways*". Science 305 (5687): 1163-1167.)

Therapies targeting EGFR have been developed. For example, cetuximab (ERBITUX™) and panitumumab (VECTIBIX™) are anti-EGFR antibodies. Erlotinib (TARCEVA™) and gefitinib (IRESSA™) are quinazolines useful as orally active selective inhibitors of EGFR tyrosine kinase. These drugs are most effective in patients whose cancers are driven by aberrant EGFR activity. A randomized, large-scale, double-blinded study of IRESSA™ (IRESSA Pan-Asia Study (IPASS)) compared gefitinib to the traditional chemotherapy as a first-line treatment in non-small cell lung cancer (NSCLC). (Mok et al. (2009) "*Gefitinib or carboplatin paclitaxel in pulmonary adenocarcinoma*." N Eng J Med 361:947-957)). IPASS studied 1,217 patients with confirmed adenocarcinoma histology. The study revealed that progression-free survival (PFS) was significantly longer for IRESSA" than chemotherapy in patients with EGFR mutation-positive tumors. The opposite was true for tumors where EGFR was not mutated: PFS was significantly longer for chemotherapy than IRESSA™. The study demonstrated that to improve a lung cancer patient's chances of successful treatment, EGFR mutation status must be known.

Analysis of clinical outcome revealed that patients with tumors harboring mutations in the kinase domain of EGFR (exons 18-21) have better response to erlotinib than those with tumors expressing wild-type EGFR. (U.S. Pat. Nos. 7,294,468 and 7,960,118) These mutations are predictive of response to tyrosine kinase inhibitors (TKIs) such as quinazolines erlotinib (TARCEVA™) and gefitinib (IRESSA™). Among the EGFR mutations, deletion of amino acids 746-750 is especially common in lung cancer patients (see U.S. Pat. No. 7,294,468 and Kosaka et al. (2004) "*Mutations of the epidermal growth factor receptor gene in lung cancer, biological and clinical implications*." Cancer Res. 64:8919-23.) Kosaka et al. document a study involving 277 Japanese lung caner patients. The Japanese study revealed that EGFR mutations occurred in 40% of adenocarcinomas of the lung. About one-half of the mutations (20% of patients) are deletions around amino acids 746-750 (nucleotides 2238-2250).

Some mutations in the EGFR kinase domain are common, while others occur less frequently. However, it is essential that a clinical test for EGFR mutations target as many mutations as possible. This will assure that patients with rare mutations do not receive a "false negative" test result. If a rare mutation goes undetected, the patient with such a mutation will not receive potentially life-saving treatment. Therefore when a new mutation in the EGFR kinase domain is discovered, detecting this mutation has the potential of affecting the clinical outcome in some patients.

SUMMARY OF THE INVENTION

In one embodiment, the invention is an oligonucleotide that specifically hybridizes to a nucleic acid containing a mutation selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1.

In another embodiment, the invention is a method of detecting a mutation in the epidermal growth factor receptor (EGFR) gene in a sample from a human, comprising: contacting the nucleic acid in the sample with an oligonucleotide capable of selectively hybridizing to a target nucleic acid containing a mutation selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1; incubating the sample under conditions allowing selective hybridization of the oligonucleotide to the target nucleic acid; and detecting the hybridization.

In yet another embodiment, the invention is a method of treating a patient having a tumor possibly harboring cells with a mutation in the epidermal growth factor receptor (EGFR) gene, comprising requesting that the patient's sample be tested for the presence of the mutated EGFR gene characterized by a mutation selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1; and if any of the mutations are reported as present, administering to the patient a compound that inhibits signaling of the mutant EGFR protein encoded by the mutated gene.

In yet another embodiment, the invention is a kit for detecting mutations in the human EGFR gene, including any mutation selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1, the kit comprising one or more oligonucleotides selected from SEQ ID NOs: 11-40.

In yet another embodiment, the invention is a reaction mixture for detecting mutations in the human EGFR gene, including any mutation selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1, the reaction mixture comprising one or more oligonucleotides selected from SEQ ID NOs: 11-40.

In yet another embodiment, the invention is the use of oligonucleotides selected from SEQ ID NOs: 11-40 in detecting mutations in the human EGFR gene selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1. In a variation of this embodiment, the invention is the use of detection of the mutations in the human EGFR gene selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1, in diagnosis or prognosis of cancer. In a further variation of this embodiment, the invention is the use of detection of the mutations in the human EGFR gene selected from the list consisting of 2236_2248>ACCC, 2237_2244>CGCCC, 2252_2277>AC, 2240_2264>CGAAAGA, 2239_2240 TT>CC and 2264 C>A in SEQ ID NO: 1 in designing treatment of a cancer patient or predicting response of the cancer patient to the treatment.

BRIEF DESCRIPTION OF THE DRAWINGS

FIG. 1 (1A-1C) shows SEQ ID NO: 1, the cDNA sequence of wild-type EGFR.

FIG. 2 shows SEQ ID NO: 2, the amino acid sequence of wild-type EGFR.

FIG. 3 shows SEQ ID NO: 3, the wild-type sequence of nucleotides 2221-2260 of the EGFR gene; and SEQ ID NO: 4, the mutation 2236_2248>ACCC.

FIG. 4 shows SEQ ID NO: 3, the wild-type sequence of nucleotides 2221-2260 of the EGFR gene; and SEQ ID NO: 5, the mutation 2237_2244>CGCCC.

FIG. 5 shows SEQ ID NO: 6, the wild-type sequence of nucleotides 2221-2280 of the EGFR gene; and SEQ ID NO: 7, the mutation 2252_2277>AC.

FIG. 6 shows SEQ ID NO: 6, the wild-type sequence of nucleotides 2221-2280 of the EGFR gene; and SEQ ID NO: 8, the mutation 2240_2264>CGAAAGA.

FIG. 7 shows SEQ ID NO: 3, the wild-type sequence of nucleotides 2221-2260 of the EGFR gene; and SEQ ID NO: 9, the mutation 2239_2240 TT>CC.

FIG. 8 shows SEQ ID NO: 6, the wild-type sequence of nucleotides 2221-2280 of the EGFR gene; and SEQ ID NO: 10, the mutation 2264 C>A.

DETAILED DESCRIPTION OF THE INVENTION

Definitions

To facilitate the understanding of this disclosure, the following definitions of the terms used herein are provided.

The term "n_m" or "n-m del" refers to a mutation that results in a nucleic acid lacking the nucleotides between positions "n" and "m." The term "n_m>XYZ" refers to a complex mutation where the nucleic acid is lacking nucleotides between positions "n" and "m," but nucleotide sequence XYZ is inserted in their place. For example, the term "2236_2248>ACCC" refers to a mutation that results in a nucleic acid lacking nucleotides 2236-2248 but the nucleotide sequence ACCC is inserted in the place of the deleted nucleotides.

The term "nX>Y" refers to a mutation that results in a substitution of nucleotide X at position "n" with the nucleotide Y. For example, the term "2264C>A" refers to a mutation that results in a substitution of a cytosine at position 2264 with an adenine. Similarly, the term "2239_2240TT>CC" refers to a mutation that results in a substitution of two thymines at positions 2239 and 2240 with two cytosines.

The term "allele-specific primer" or "AS primer" refers to a primer that hybridizes to more than one variant of the target sequence, but is capable of discriminating between the variants of the target sequence in that only with one of the variants, the primer is efficiently extended by the nucleic acid polymerase under suitable conditions. With other variants of the target sequence, the extension is less efficient, inefficient or undetectable.

The term "common primer" refers to the second primer in the pair of primers that includes an allele-specific primer. The common primer is not allele-specific, i.e. does not discriminate between the variants of the target sequence between which the allele-specific primer discriminates.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e. there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

The term "sample" refers to any composition containing or presumed to contain nucleic acid. This includes a sample of tissue or fluid isolated from an individual for example, skin, plasma, serum, spinal fluid, lymph fluid, synovial fluid, urine, tears, blood cells, organs and tumors, and also to samples of in vitro cultures established from cells taken from an individual, including the formalin-fixed paraffin embedded tissues (FFPET) and nucleic acids isolated therefrom.

The terms "polynucleotide" and "oligonucleotide" are used interchangeably. "Oligonucleotide" is a term sometimes used to describe a shorter polynucleotide. An oligonucleotide may be comprised of at least 6 nucleotides, for example at least about 10-12 nucleotides, or at least about 15-30 nucleotides corresponding to a region of the designated nucleotide sequence.

The term "primary sequence" refers to the sequence of nucleotides in a polynucleotide or oligonucleotide. Nucleotide modifications such as nitrogenous base modifications, sugar modifications or other backbone modifications are not a part of the primary sequence. Labels, such as chromophores conjugated to the oligonucleotides are also not a part of the primary sequence. Thus two oligonucleotides can share the same primary sequence but differ with respect to the modifications and labels.

The term "primer" refers to an oligonucleotide which hybridizes with a sequence in the target nucleic acid and is capable of acting as a point of initiation of synthesis along a complementary strand of nucleic acid under conditions suitable for such synthesis. As used herein, the term "probe" refers to an oligonucleotide which hybridizes with a sequence in the target nucleic acid and is usually detectably labeled. The probe can have modifications, such as a 3'-terminus modification that makes the probe non-extendable by nucleic acid polymerases, and one or more chromophores. An oligonucleotide with the same sequence may serve as a primer in one assay and a probe in a different assay.

As used herein, the term "target sequence", "target nucleic acid" or "target" refers to a portion of the nucleic acid sequence which is to be either amplified, detected or both.

The terms "hybridized" and "hybridization" refer to the base-pairing interaction of between two nucleic acids which results in formation of a duplex. It is not a requirement that two nucleic acids have 100% complementarity over their full length to achieve hybridization.

The terms "selective hybridization" and "specific hybridization" refer to the hybridization of a nucleic acid predominantly (50% or more of the hybridizing molecule) or nearly exclusively (90% or more of the hybridizing molecule) to a particular nucleic acid present in a complex mixture where other nucleic acids are also present. For example, under typical PCR conditions, primers specifically hybridize to the target nucleic acids to the exclusion of non-target nucleic acids also present in the solution. The specifically hybridized primers drive amplification of the target nucleic acid to produce an amplification product of the target nucleic acid that is at least the most predominant amplification product and is preferably the nearly exclusive (e.g., representing 90% or more of all amplification products in the sample) amplification product. Preferably, the non-specific amplification product is present in such small amounts that it is either non-detectable or is detected in such small amounts as to be easily distinguishable from the specific amplification product. Similarly, probes specifically hybridize to the target nucleic acids to the exclusion of non-target nucleic acids also present in the reaction mixture. The specifically hybridized probes allow specific detection of the target nucleic acid to generate a detectable signal that is at least the most predominant signal and is preferably the nearly exclusive (e.g., representing 90% or more of all amplification products in the sample) signal.

The present invention describes a novel mutation in the EGFR kinase domain that is useful for cancer diagnosis and prognosis, designing a therapy regimen and predicting success of the therapy.

The nucleotide numbering used herein is in reference to SEQ ID NO: 1, shown on FIG. 1. Within SEQ ID NO: 1, the portion of the sequence between nucleotides 2221 and 2280, that encompasses the six mutations described herein is highlighted and underlined.

The amino acid numbering used herein is in reference to SEQ ID NO: 2, shown on FIG. 2. Within SEQ ID NO: 2, the signal sequence includes amino acids 1-24, the extracellular domain includes amino acids 24-645, the transmembrane domain includes amino acids 646-668, and the cytoplasmic domain includes amino acids 669-1210, of which the tyrosine kinase domain is amino acids 718-964, and the threonine phosphorylation site is amino acid 678.

The present study identified six novel mutations in the exon 19 (portion of the kinase domain) of the human EGFR gene. The mutations are illustrated in FIGS. 3-8. In the figures, the sequence deleted from the wild-type gene is underlined. The sequence inserted in the mutant gene in place of the deletion is shown in bold italics. The mutations are also summarized in Table 1.

TABLE 1

New mutations and wild-type sequences in exon 19 of the human EGFR gene

| SEQ ID NO: | | NUCLEOTIDE SEQUENCE |
|---|---|---|
| 3 | WT 2221-2260 | CCCGTCGCTATCAAGGAATTAAGAGAAGCAACATCTCCGA |
| 4 | Mut 2236_2248 > ACCC | CCCGTCGCTATCAAG*ACCC*CAACATCTCCGA |
| 5 | Mut 2237_2244 > CGCCC | CCCGTCGCTATCAAGG*CGCCC*GAAGCAACATCTCCGA |
| 6 | WT 2221-2280 | CCCGTCGCTATCAAGGAATTAAGAGAAGCAACATCTCCGAAAGCCAACAAGGAAATCCTC |
| 7 | Mut 2252_2277 > AC | CCCGTCGCTATCAAGGAATTAAGAGAAGCAA*AC*CTC |
| 8 | Mut 2240-2264 > CGAAAGA | CCCGTCGCTATCAAGGAAT*CGAAAGA*CAACAAGGAAATCCTC |
| 9 | Mut 2239_2240 TT > CC | CCCGTCGCTATCAAGGAA*CC*AAGAGAAGCAACATCTCCGA |
| 10 | Mut 2264 C > A | CCCGTCGCTATCAAGGAATTAAGAGAAGCAACATCTCCGAAAG*A*CAACAAGGAAATCCTC |

The first mutation 2236_2248>ACCC is shown on FIG. 3. FIG. 3 shows the fragment of the nucleotide sequence of the wild-type EGFR (SEQ ID NO: 3) and the corresponding fragment encoding the mutation 2236_2248>ACCC (SEQ ID NO: 4).

The second mutation 2237_2244>CGCCC is shown on FIG. 4. FIG. 4 shows the fragment of the nucleotide sequence of the wild-type EGFR (SEQ ID NO: 3) and the corresponding fragment encoding the mutation 2237_2244>CGCCC (SEQ ID NO: 5).

The third mutation 2252_2277>AC is shown on FIG. 5. FIG. 5 shows the fragment of the nucleotide sequence of the wild-type EGFR (SEQ ID NO: 6) and the corresponding fragment encoding the mutation 2252_2277>AC (SEQ ID NO: 7).

The fourth mutation 2240-2264>CGAAAGA is shown on FIG. 6. FIG. 6 shows the fragment of the nucleotide sequence of the wild-type EGFR (SEQ ID NO: 6) and the corresponding fragment encoding the mutation 2240-2264>CGAAAGA (SEQ ID NO: 8).

The fifth mutation 2239_2240 TT>CC is shown on FIG. 7. FIG. 7 shows the fragment of the nucleotide sequence of the wild-type EGFR (SEQ ID NO: 3) and the corresponding fragment encoding the mutation 2239_2240 TT>CC (SEQ ID NO: 9).

The sixth mutation 2264 C>A is shown on FIG. 8. FIG. 8 shows the fragment of the nucleotide sequence of the wild-type EGFR (SEQ ID NO: 6) and the corresponding fragment encoding the mutation 2264 C>A (SEQ ID NO: 10).

In one embodiment, the present invention comprises oligonucleotides for detecting mutations in exon 19 of EGFR selected from the list consisting of 2236_2248>ACCC, 2237_2244>CGCCC, 2252_2277>AC, 2240-2264>CGAAAGA, 2239_2240 TT>CC and 2264 C>A in SEQ ID NO: 1. In one embodiment, the invention comprises oligonucleotides (SEQ ID NOs: 11-40) for detecting the above mentioned mutations by allele-specific PCR (Tables 2). (Allele-specific PCR has been described in U.S. Pat. No. 6,627,402). As indicated in Table 2, oligonucleotides SEQ ID NOs: 12-14, 17-20, 23-25, 28-30, 33-35, 37 and 38 are selective, i.e. allele-specific primers. Some of these allele-specific primers contain internal mismatches with both the wild-type and mutant target sequence. Additional mismatches in allele-specific PCR primers have been shown to increase selectivity of the primers. See U.S. patent application Ser. No. 12/582,068 filed on Oct. 20, 2009, which is incorporated herein by reference in its entirety. Other oligonucleotides in Table 2, SEQ ID NOs: 11, 15, 16, 21, 26, 27, 31, 32 and 36 are not selective, i.e. not allele-specific. These oligonucleotides direct amplification of both mutant and wild-type template. These selective and non-selective primers of the present invention are arbitrarily designated as "forward" primers. For exponential amplification, these primers may be paired with a second "reverse" primer that is not allele-specific, e.g. SEQ ID NO: 40. For probe based detection, a probe, e.g. SEQ ID NO: 39 may be used. It is understood by one of skill in the art that SEQ ID NOs: 39 and 40 are non-limiting examples. A different reverse primer and a different probe may also be used with a forward primer selected from SEQ ID NOs: 11-40.

TABLE 2

Oligonucleotides for detecting new mutations in exon 19 of EGFR

| Description | SEQ ID NO: | Sequence 5'-3' |
|---|---|---|
| Mutation 2240_2264 > CGAAAGA | | |
| Common Forward Primer | 11 | AATTCCCGTCGCTATCAAGGAA |
| Selective Forward Primer | 12 | TTCCCGTCGCTATCAAGGAATC |
| Selective Forward Primer | 13 | CCGTCGCTATCAAGGAATCGAA |
| Selective Forward Primer | 14 | GTCGCTATCAAGGAATCGAAAGACAA |
| Common Forward Primer | 15 | CAACAAGGAAATCCTCGATGTGAGT |
| Mutation 2252_2277 > AC | | |
| Common Forward Primer | 16 | GTCGCTATCAAGGAATTAAGAGAAGCA |
| Selective Forward Primer | 17 | GTCGCTATCAAGGAATTAAGAGAAGCAAA |
| Selective Forward Primer | 18 | CGCTATCAAGGAATTAAGAGAAGCAAAC |
| Selective Forward Primer | 19 | CTATCAAGGAATTAAGAGAAGCAAACCT |
| Selective Forward Primer | 20 | CTATCAAGGAATTAAGAGAAGCAAACCTC |
| Common Forward Primer | 21 | TCGATGTGAGTTTCTGCTTTGCT |
| Mutation 2236_2248 > ACCC | | |
| Common Forward Primer | 22 | AAAGTTAAAATTCCCGTCGCTATCAA |
| Selective Forward Primer | 23 | AGTTAAAATTCCCGTCGCTATCAAGA |
| Selective Forward Primer | 24 | GTTAAAATTCCCGTCGCTATCAAGAC |
| Selective Forward Primer | 25 | CCGTCGCTATCAAGACCCCA |
| Common Forward Primer | 26 | CAACATCTCCGAAAGCCAACAA |

TABLE 2-continued

Oligonucleotides for detecting new mutations in exon 19 of EGFR

| Description | SEQ ID NO | Sequence 5'-3' |
|---|---|---|
| Mutation 2237_2244 > CGCCC | | |
| Common Forward Primer | 27 | AAAGTTAAAATTCCCGTCGCTATCAA |
| Selective Forward Primer | 28 | AAGTTAAAATTCCCGTCGCTATCAAGGC |
| Selective Forward Primer | 29 | CCGTCGCTATCAAGGCGC |
| Selective Forward Primer | 30 | CGCTATCAAGGCGCCCGA |
| Common Forward Primer | 31 | GAAGCAACATCTCCGAAAGCCAACAAGGA |
| Mutation 2264C > A | | |
| Common Forward Primer | 32 | GGAATTAAGAGAAGCAACATCTCCGAA |
| Selective Forward Primer | 33 | ATTAAGAGAAGCAACATCTCCGAAAGA |
| Selective Forward Primer | 34 | ATTAAGAGAAGCAACATCTCCGAA<u>F</u>GA |
| Selective Forward Primer | 35 | ATTAAGAGAAGCAACATCTCCGAA<u>F</u>GAC |
| Mutation 2239_2240TT > CC | | |
| Common Forward Primer | 36 | TTAAAATTCCCGTCGCTATCAAGGA |
| Selective Forward Primer | 37 | TAAAATTCCCGTCGCTATCAAGGAAC |
| Selective Forward Primer | 38 | AATTCCCGTCGCTATCAAGGAACC |
| Additional oligonucleotides | | |
| Probe | 39 | <u>M</u>ATGGCTC<u>Q</u>TGAACCTCAGGCCCACCTTT<u>P</u> |
| Reverse Primer | 40 | AGAGCAGAGCAGCTGCCAGA |

Common primer = a primer that amplifies both mutant and wild-type nucleic acid
Selective primer = a primer that amplifies only the mutant and not the wild-type nucleic acid
<u>E</u> = N4-tert-butyl-benzyl-dC
<u>F</u> = N6-tert-butyl-benzyl-dA
<u>M</u> = FAM
<u>Q</u> = BHQ2
<u>P</u> = phosphate For successful extension of a primer, the primer needs to have at least partial complementarity to the target sequence. Generally, complementarity at the 3'-end of the primer is more critical than complementarity at the 5'-end of the primer. (Innis et al. Eds. *PCR Protocols*, (1990) Academic Press, Chapter 1, pp. 9-11). This means that variations of the 5'-end, i.e. additions, substitutions or removal of nucleotides at the 5'-end, do not affect performance of a primer in a PCR assay. Therefore the present invention encompasses the primers disclosed in Tables 2 as well as the variants of these primers with 5'-end variations.

Similarly, for successful probe hybridization, the probe needs to have at least partial complementarity to the target sequence. Generally, complementarity close to the central portion of the probe is more critical than complementarity at the ends of the probe. (Innis et al. Chapter 32, pp. 262-267). This means that variations of the ends of the probe, i.e. additions, substitutions or removal of a few nucleotides, do not affect performance of the probe in hybridization. Therefore the present invention encompasses the probe disclosed in Table 2 as well as the variants of these probes with terminal variations.

In other variations of this embodiment, the probe has a particular structure, including a protein-nucleic acid (PNA), a locked nucleic acid (LNA), a molecular beacon probe (Tyagi et al. (1996) Nat. Biotechnol. 3:303-308) or SCORPIONS® self-probing primers (Whitcombe et al. (1999) Nat. Biotechnol. 8:804-807). A probe may be labeled with a radioactive, a fluorescent or a chromophore label. For example, the mutations may be detected by real-time allele-specific polymerase chain reaction, where hybridization of a probe to the amplification product results in enzymatic digestion of the probe and detection of the digestion products (TaqMan™ probe, Holland et al. (1991) P.N.A.S. USA 88:7276-7280). Hybridization between the probe and the target may also be detected by detecting the change in fluorescence due to the nucleic acid duplex formation. (U.S. application Ser. No. 12/330,694, filed on Dec. 9, 2008) or by detecting the characteristic melting temperature of the hybrid between the probe and the target (U.S. Pat. No. 5,871,908).

Mutant EGFR gene or gene product can be detected in tumors or other body samples such as urine, sputum or serum. The same techniques discussed above for detection of mutant EGFR genes or gene products in tumor samples can be applied to other body samples. For example, cancer cells are sloughed off from tumors and appear in such body samples. State of the art nucleic acid detection methods are capable of detecting mutant cells in a background of non-tumor cells in a wide variety of sample types.

In another embodiment, the invention is a method of treating a patient having a tumor possibly harboring cells with an EGFR gene having mutations in exon 19, selected from the group consisting of 2236_2248>ACCC, 2237_2244>CGCCC, 2252_2277>AC, 2240-2264>CGAAAGA, 2239_2240 TT>CC and 2264 C>A in SEQ ID NO: 1; the method comprising requesting that the patient be tested for one or more of the above mentioned mutations in the patient's sample, and if the mutation is detected, administering to the patient a tyrosine kinase inhibitor (TKI) or an EGFR inhibitor. In variations of this embodiment, the tyrosine kinase inhibitors are EGFR kinase inhibitors such as for example, cetuximab, panitumumab, erlotinib or gefitinib.

In a variation of this embodiment, the method further comprises querying for one more of the following mutations: G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, D770-N771 del NPG ins, D770-N771 del SVD ins, P772-H773 dup, P772-H773 del V ins, M766-A767 del AI ins, S768-V769 del SVA ins, G779S, P848L, G857V, L858R, L861Q, L883S, D896Y, and E746-A750 del AP ins; and if one or more of the mutations are present, administering to the patient a compound that inhibits signaling of the mutant EGFR protein encoded by the mutated gene. The nucleotide changes causing the mutations listed above and methods of detecting them are disclosed in U.S. Pat. Nos. 7,294,468 and 7,960,118 and U.S. application Ser. No. 13/280,976, filed on Oct. 25, 2011 (mutation E746-A750 del AP ins). Multiple mutations can be detected simultaneously or separately by using hybridization to multiple probes, for example in a dot-blot or nucleic acid array format, multiplex PCR, for example multiplex allele-specific PCR and multiplex PCR followed by a probe melting assay with each probe characterized by a mutation-specific melting temperature. Multiple mutations may also be detected by high-throughput sequencing for example, using a method involving emulsion PCR amplification of single molecules adhered to a solid support, subsequent sequencing by synthesis and bioinformatic analysis of the sequence data, such as the method developed by 454 Life Sciences, Inc. (Branford, Conn).

In another embodiment, the invention is a method of determining an altered response of a patient having a malignant tumor to tyrosine kinase inhibitors (TKIs) or EGFR inhibitors. The method comprises querying the patient's sample for the presence of one or more mutations in exon 19 of EGFR selected from the group consisting of 2236_2248>ACCC, 2237_2244>CGCCC, 2252_2277>AC, 2240-2264>CGAAAGA, 2239_2240 TT>CC and 2264 C>A in SEQ ID NO: 1; and if the mutation is found, determining that the treatment is likely to be successful. In variations of this embodiment, the tyrosine kinase inhibitors are EGFR kinase inhibitors or EGFR inhibitors are, for example, cetuximab, panitumumab, erlotinib or gefitinib.

In a variation of this embodiment, the method further comprises querying for one more of the following mutations: G719A, G719C, K745-A750 del K ins, E746V, E746K, L747S, E749Q, A750P, A755V, S768I, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, D770-N771 del NPG ins, D770-N771 del SVD ins, P772-H773 dup, P772-H773 del V ins, M766-A767 del AI ins, S768-V769 del SVA ins, G779S, P848L, G857V, L858R, L861Q, L883S, D896Y and and E746-A750 del AP ins; and if one or more of the mutations are present, determining that the treatment with tyrosine kinase inhibitors is likely to be successful.

In yet another embodiment, the invention is a kit containing reagents necessary for detecting the one or more mutations in exon 19 of EGFR selected from the group consisting of 2236_2248>ACCC, 2237_2244>CGCCC, 2252_2277>AC, 2240-2264>CGAAAGA, 2239_2240 TT>CC and 2264 C>A in SEQ ID NO: 1. The kit may comprise oligonucleotides such as probes or amplification primers specific for the mutated sequence but not the wild type sequence. Optionally, one or more allele-specific primers, common primers and probes in the kit may be selected from Tables 2. The kit further comprises reagents necessary for the performance of amplification and detection assay, such as the components of PCR, a real-time PCR, or transcription mediated amplification (TMA). In some embodiments, the mutation-specific oligonucleotide is detectably labeled. In such embodiments, the kit comprises reagents for labeling and detecting the label. For example, if the oligonucleotide is labeled with biotin, the kit may comprise a streptavidin reagent with an enzyme and its chromogenic substrate. In variations of this embodiment, the kit further includes reagents for detecting at least one more mutation in the EGFR gene, selected from the following: G719A, G719C, K745-A750 del K ins, E746V, E746K, L747S, E749Q, A750P, A755V, S7681, L858P, L858R, E746-R748 del, E746-S752 del V ins, L747-E749 del, L747-A750 del P ins, L747-T751 del, L747-T751 del P ins, L747-P753 del S ins, L747-S752 del, R748-P753 del, T751-I759 del T ins, S752-I759 del, P753-K757 del, D770-N771 del NPG ins, D770-N771 del SVD ins, P772-H773 dup, P772-H773 del V ins, M766-A767 del AI ins, S768-V769 del SVA ins, G779S, P848L, G857V, L858R, L861Q, L883S, D896Y and and E746-A750 del AP ins.

In yet another embodiment, the invention is a reaction mixture for detecting mutations in the human EGFR gene, including one or more mutations selected from the list consisting of 2236_2248>ACCC, 2237_2244>CGCCC, 2252_2277>AC, 2240-2264>CGAAAGA, 2239_2240 TT>CC and 2264 C>A in SEQ ID NO: 1, the reaction mixture comprising one or more oligonucleotides selected from SEQ ID NOs: 11-40.

In yet another embodiment, the invention is the use of oligonucleotides selected from SEQ ID NOs: 11-40 in detecting one or more mutations selected from the list consisting of 2236_2248>ACCC, 2237_2244>CGCCC, 2252_2277>AC, 2240-2264>CGAAAGA, 2239_2240 TT>CC and 2264 C>A in SEQ ID NO: 1. In a variation of this embodiment, the invention is the use of detection of one or more mutations selected from the list consisting of 2236_2248>ACCC, 2237_2244>CGCCC, 2252_2277>AC, 2240-2264>CGAAAGA, 2239_2240 TT>CC and 2264 C>A in SEQ ID NO: 1, in diagnosis or prognosis of cancer. In a further variation of this embodiment, the invention is the use of detection of one or more mutations selected from the list consisting of 2236_2248>ACCC, 2237_2244>CGCCC, 2252_2277>AC, 2240-2264>CGAAAGA, 2239_2240 TT>CC and 2264 C>A in SEQ ID NO: 1 in designing treatment of a cancer patient or predicting response of the cancer patient to the treatment.

EXAMPLE 1

Identifying Mutations in Lung Cancer Patient Samples

Tissue samples were obtained from lung cancer (NSCLC) patients. The samples were preserved as formalin-fixed, paraffin embedded tissue (FFPET). Nucleic acids were isolated from the samples and subjected to direct sequencing on the Genome Sequencer FLX instrument (454 Life Sciences, Branford, Conn.).

The 2236_2248>ACCC mutation was detected in the average of 24.6% of the total of 3,550 reads from a sample. The 2237_2244>CGCCC mutation was detected in the average of 27.7% of the total of 4205 reads from a sample. The 2252_2277>AC mutation was detected in the average of 24.6% of the total of 5368 reads from a sample. The 2240-2264>CGAAAGA mutation was detected in the average of 32.2% of the total of 3394 reads from a sample. The 2239_2240 TT>CC mutation was detected in the average of 74.3% of the total of 3120 reads from a sample. The 2264 C>A mutation was detected in the average of 32.8% of the total of 3394 reads from a sample. Only fraction of the reads was found to contain a mutation reflecting the fact that the samples are mixtures of tumor and non-tumor cells.

EXAMPLE 2

Detecting the Mutations Using Allele-specific Oligonucleotides

In this example, the mutant and wild-type targets were represented by plasmids containing the mutant and wild-type inserts respectively. The targets were amplified using either mutation-specific primers or, in control reactions, non-selective "common" primers.

Each 15 µl reaction contained 10,000 copies of the target DNA and standard PCR reagents including nucleoside triphosphates, DNA polymerase, uracil-N-glycosylase, and 0.1 µM each of forward and reverse primer, and 0.05 µM probe (all selected from Table 2), Amplification and analysis were done using the LightCycler™ 480 instrument (Roche Applied Science, Indianapolis, Ind.) Reactions were cycled using the following profile: 50° C. for 5 minutes, followed by 2 cycles of 95° C. for 10 seconds and 62° C. for 30 seconds, followed by 55 cycles of 93° C. for 10-seconds and 62° C. for 30 seconds.

Results for each forward primer are shown in Table 3. Amplification is represented by "cycles to threshold" or $C_t$ value. The higher $C_t$ represents a less efficient amplification, e.g. by a mismatched primer. $\Delta C_t$ represents the difference between the wild-type and the mutant target amplification. The presence of $\Delta C_t$ indicates that the mutation is detected and the value of $\Delta C_t$ represents selectivity of the assay.

TABLE 3

Detecting mutations by allele-specific PCR

| FWD PRIMER SEQ ID NO: | mut $C_t$* | wt $C_t$ | $\Delta C_t$ |
|---|---|---|---|
| Mutation 2240_2264 > CGAAAGA | | | |
| 11 | 22.2 | 22.6 | 0.4 |
| 12 | 22.3 | 30.1 | 7.8 |
| 13 | 22.5 | 36.7 | 14.2 |
| 14 | 21.9 | 33.1 | 11.3 |
| 15 | 22.5 | 22.5 | 0 (control) |
| Mutation 2252_2277 > AC | | | |
| 16 | 22.1 | 22.5 | 0.4 (control) |
| 17 | 22.2 | 22.6 | 0.4 (control) |
| 18 | 24.5 | 39.4 | 14.9 |
| 19 | 22.3 | 27.7 | 5.4 |
| 20 | 22.6 | 29.5 | 6.9 |
| 21 | 21.2 | 22.3 | 1.1 (control) |

TABLE 3-continued

Detecting mutations by allele-specific PCR

| FWD PRIMER SEQ ID NO: | mut $C_t$* | wt $C_t$ | $\Delta C_t$ |
|---|---|---|---|
| Mutation 2236_2248 > ACCC | | | |
| 22 | 22.8 | 23.0 | 0.2 (control) |
| 23 | 22.6 | 29.8 | 7.2 |
| 24 | 22.5 | 47.4 | 24.9 |
| 25 | 22.7 | NA | >32.3 |
| 26 | 22.4 | 22.4 | 0 (control) |
| Mutation 2237_2244 > CGCCC | | | |
| 27 | 23.1 | 22.9 | −0.2 (control) |
| 28 | 22.7 | 28.4 | 5.6 |
| 29 | 22.6 | NA | >32.4 |
| 30 | 22.4 | NA | >32.6 |
| 31 | 22.8 | 23.0 | 0.2 (control) |
| Mutation 2264C > A | | | |
| 32 | 23.1 | 23.0 | −0.1 (control) |

TABLE 3-continued

Detecting mutations by allele-specific PCR

| FWD PRIMER SEQ ID NO: | mut $C_t$* | wt $C_t$ | $\Delta C_t$ |
|---|---|---|---|
| 33 | 23.5 | 39.0 | 15.5 |
| 34 | 24.7 | NA | >30.3 |
| 35 | 24.8 | 36.5 | 11.7 |
| Mutation 2239_2240TT > CC | | | |
| 36 | 22.2 | 22.8 | 0.6 (control) |
| 37 | 22.5 | 25.3 | 2.8 |
| 38 | 22.4 | 38.0 | 15.5 |

*each $C_t$ is an average of two experiments
NA: not amplified
Control—common, not allele-specific forward primer While the invention has been described in detail with reference to specific examples, it will be apparent to one skilled in the art that various modifications can be made within the scope of this invention. Thus the scope of the invention should not be limited by the examples described herein, but by the claims presented below.

What is claimed is:

1. A method of detecting a 2236_2248>ACCC mutation in the epidermal growth factor receptor (EGFR) sequence of SEQ ID NO:1 in a sample comprising nucleic acid from a human, comprising:
 (a) contacting the nucleic acid in the sample with at least one allele-specific primer having a sequence selected from SEQ ID NOs: 23-25;
 (b) incubating the nucleic acid and at least one allele-specific primer and amplifying the target nucleic acid, wherein amplification results from extension of the allele-specific primer if the target nucleic acid contains a 2236_2248>ACCC mutation in the EGFR sequence of SEQ ID NO:1, and
 (c) detecting the 2236_2248>ACCC mutation in the EGFR sequence of SEQ ID NO: 1 by detecting the amplification in step (b).

2. The method of claim 1, wherein the sample is derived from a human patient having a tumor.

3. The method of claim 1, wherein the human has cancer.

4. The method of claim 1, wherein the human is a patient who is a candidate for treatment with a compound that inhibits signaling of the mutant EGFR protein.

* * * * *